United States Patent
Moser et al.

(10) Patent No.: US 11,377,448 B2
(45) Date of Patent: Jul. 5, 2022

(54) CRYSTALLINE SODIUM SALT OF 5-METHYL-(6S)-TETRAHYDROFOLIC ACID

(71) Applicant: MERCK PATENT GMBH, Darmstadt (DE)

(72) Inventors: Rudolf Moser, Schaffhausen (CH); Viola Groehn, Dachsen (CH); Fritz Blatter, Reinach (CH); Martin Szelagiewicz, Basel (CH); Ruth Boehni Stamm, Stein Am Rhein (CH); Markus Ruettimann, Winterthur (CH)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/499,732

(22) PCT Filed: Mar. 28, 2018

(86) PCT No.: PCT/EP2018/057905
§ 371 (c)(1),
(2) Date: Sep. 30, 2019

(87) PCT Pub. No.: WO2018/178144
PCT Pub. Date: Oct. 4, 2018

(65) Prior Publication Data
US 2021/0107902 A1    Apr. 15, 2021

(30) Foreign Application Priority Data

Mar. 31, 2017 (EP) ..................................... 17164365

(51) Int. Cl.
C07D 475/04    (2006.01)

(52) U.S. Cl.
CPC ........ *C07D 475/04* (2013.01); *C07B 2200/13* (2013.01)

(58) Field of Classification Search
CPC .......................... C07D 475/04; C07B 2200/13
See application file for complete search history.

(56) References Cited

U.S. PATENT DOCUMENTS

| | | |
|---|---|---|
| 5,124,452 A | 6/1992 | Gennari |
| 5,457,202 A | 10/1995 | Scheib et al. |
| 5,719,045 A | 2/1998 | Heveling et al. |
| 5,817,659 A | 10/1998 | Muller et al. |
| 6,011,040 A | 1/2000 | Muller et al. |
| 6,441,168 B1 | 8/2002 | Müller et al. |
| 6,596,721 B2 | 7/2003 | Müller et al. |
| 9,150,982 B2 | 10/2015 | Wang et al. |
| 2017/0129893 A1 | 5/2017 | Sethi et al. |

FOREIGN PATENT DOCUMENTS

| | | | |
|---|---|---|---|
| CN | 104557937 A | | 4/2015 |
| EA | 017742 B1 | | 2/2013 |
| JP | H11116482 A | | 4/1999 |
| JP | 2000327680 A | | 11/2000 |
| JP | 2015506941 A | | 3/2015 |
| RU | 2165422 C2 | | 4/2001 |
| RU | 2187508 C2 | | 8/2002 |
| WO | WO 2013025203 | * | 2/2013 |
| WO | 2015193778 A1 | | 12/2015 |

OTHER PUBLICATIONS

Yaws. Waste Management, 1998, 17(8), 541-547 (Year: 1998).*
STN HCAPLUS record of Bhanu WO 2013023203, published Feb. 21, 2013, accessed Feb. 20, 2021 (Year: 2013).*
Folstein. American Journal of Psychiatry, 2007, 164, 861-867 (Year: 2007).*
Herrmann. Clinical Chemistry and Laboratory Medicine, 2005, 43(10), 1111-1117 (Year: 2005).*
Sala. Dementia and Geriatric Cognitive Disorders, 2008, 26, 506-512 (Year: 2008).*
Ganguly. Nutrition Journal, 2015, 14:6, 1-10 (Year: 2015).*
Gopinath. Archives of Internal Medicine, 2009, 169 (9), 901-902 (Year: 2009).*
Imbard. International Journal of Environmental Research and Public Health, 2013, 10, 4352-4389 (Year: 2013).*
International Search Report PCT/EP2018/057905 dated Jun. 4, 2018 (pp. 1-3).
Dr. Marco Taddei; Fundamentals And Applications of X-Ray Diffraction with emphasis on Powder X-Ray Diffraction ; date: unknown (p. 1-95).
Office Action in corresponding CN 201880021316.5 dated Jan. 6, 2022 (pp. 3-10).
Berstein, J., ,,Polimorfizm molekulârnyh kritallov [Polymorphism in Molecular Crystals] Moscow: Nauka, 2007, Ch. 7.3.2 "Bioavailability", 324-330.
Kümmerer, K., "Pharmaceuticals in the Environment" Annual Review of Environment and Resources, 2010, 35, 57-75.
Morissette Sherry L. et al., "High-throughput crystallization: polymorphs, salts, co-crystals and solvates of pharmaceutical solids" Advanced Drag Delivery Reviews, 2004, 56, 275-300.
Kuznecova G. A., Methodical guidelines, Irkutsk State University, Chair for General Physics, 2005, p. 3 par. 2.
Rodriguez-Spong et al., "General principles of pharmaceutical solid polymorphism: A supramolecular perspective" Advanced Drug Delivery Reviews, 2004, 56, 241-274.
Maškovskij, M. D., Lekarstvennye sredstva [Medicaments] 14th ed., vol. 1, Moscow: Novaâ volna, 2001, p. 11.
English tranlation of Search report in corresponding Russian application 2019134064 received Jul. 21, 2021 (pp. 1-16).
Caira M.R. ed. "Crystalline Polymorphism of Organic Compounds "Topics in current Chemistry (1998) 198, 163-208.
Kawaguchi Yoko et al., Pharmaceuticals and crystallographic polymorphism, Life-Engineering Studies, 2002, vol. 4, No. 2, pp. 310-317.
Hirayama Noriaki, Organic Compound Crystal Fabrication Handbook; 2008; pp. 17-23, 37-40, 45-51, 57-65.
Search Report in corresponding Japanese Patent Application No. 2019-553844 dated Mar. 22, 2022 (pp. 1-7).

* cited by examiner

*Primary Examiner* — Noble E Jarrell
(74) *Attorney, Agent, or Firm* — Millen White Zelano and Branigan, PC; Richard Traverso

(57) ABSTRACT

The present invention is directed to a crystalline sodium salt of 5-methyl-(6S)-tetrahydrofolic acid wherein the molar ratio of 5-methyl-(6S)-tetrahydrofolic acid to sodium is from 1:1.51 to 1:2.5 and/or hydrates and/or solvates thereof, as well as, a process of obtaining the same.

22 Claims, 5 Drawing Sheets

CRYSTALLINE SODIUM SALT OF 5-METHYL-(6S)-TETRAHYDROFOLIC ACID

The present invention is directed to a crystalline sodium salt of 5-methyl-(6S)-tetrahydrofolic acid, (N-[4-[[(2-amino-1,4,5,6,7,8-hexahydro-5-methyl-4-oxo-(6S)-pteridinyl)methyl]amino]benzoyl]-L-glutamic acid, herein abbreviated as MTHF, and a process of obtaining the same.

Tetrahydrofolates are predominantly used as 5-formyltetrahydrofolic acid and the salts thereof (leucovorin and levoleucovorin), as 5-methyltetrahydrofolic acid and the salts thereof (Metafolin®), or as 5,10-methylenetetrahydrofolic acid and the salts thereof (Modufolin®) for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

5-Methyltetrahydrofolic acid is used in particular as a drug and as a food additive, as a vitamin preparation, for the prevention of neural tube defects, for the treatment of depressive illnesses, and for influencing the homocysteine level.

5-Methyltetrahydrofolic acid and salts thereof are extremely unstable and in particular are highly susceptible to oxidation [see also A. L. Fitzhugh, Pteridines 4 (4), 187-191 (1993) in this respect] and are therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid.

U.S. Pat. No. 6,441,168 B1 discloses the use of alkaline earth salts, particularly the calcium salt, used as the salts of 5-methyltetrahydrofolic acid its crystallization and its use. The crystalline calcium salts of 5-methyl-(6S)-tetrahydrofolic acid exist in four different crystalline modifications.

The drawback of the calcium salts of 5-methyl-(6S)-tetrahydrofolic acid is that they exist in four modifications, since the process of manufacturing each of which has to be controlled very precisely. Additionally, the solubility of said calcium salt of 5-methyl-(6S)-tetrahydrofolic acid in water is relatively poor, possibly leading to a reduced bioavailability and a limitation to its applicable form of use. Also a low solubility is resulting in low time-volume yields when needing to dissolve such compound for further processing e.g. a purification by recrystallization. Additionally the crystalline salts of 5-methyl-(6S)-tetrahydrofolic acid of U.S. Pat. No. 6,441,168 B1 also are having a water of crystallization of at least one equivalent per equivalent of 5-methyltetrahydrofolic acid.

New crystal forms of a pharmaceutically useful compound offer an opportunity to improve the performance profile of a pharmaceutical product. It widens the reservoir of materials a formulation scientist has available for designing new dosage forms of a drug with improved characteristics.

The technical problem underlying the present invention is the provision of a crystalline form comprising 5-methyl-(6S)-tetrahydrofolic acid which overcomes the drawbacks of the crystalline calcium salts of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

The technical problem is solved by a crystalline sodium salt of 5-methyl-(6S)-tetrahydrofolic acid wherein the molar ratio of 5-methyl-(6S)-tetrahydrofolic acid to sodium is from 1:1.51 to 1:2.5 and/or hydrates and/or solvates thereof.

The solid form of the present invention possesses improved pharmacological characteristics, for example, improved bioavailability, thus offering enhanced possibilities to modulate and design improved drug products.

Additionally the crystalline sodium salt of 5-methyl-(6S)-tetrahydrofolic acid of the present invention shows an increased solubility and especially an increased kinetic solubility against 5-methyl-(6S)-tetrahydrofolic acid and respective salts thereof known in the state of the art. The increased solubility and especially an increased kinetic solubility of the crystalline sodium salt of 5-methyl-(6S)-tetrahydrofolic acid of the present invention could lead to different processing parameters such as e.g. shorter dissolution times and thereby less oxidative stress to the product and/or finally even other application forms such as rapidly soluble powders.

Preferably, the crystalline salt has a molar ratio of 5-methyl-(6S)-tetrahydrofolic acid to sodium is from 1:1.75 to 1:2.25 and/or hydrates and/or solvates thereof.

In a further preferred embodiment, the molar ratio of 5-methyl-(6S)-tetrahydrofolic acid to sodium is approximately 1:2.

Preferably, the crystalline sodium salt of 5-methyl-(6S)-tetrahydrofolic acid is a crystalline disodium salt of 5-methyl-(6S)-tetrahydrofolic acid.

Preferably, the crystalline sodium salt of 5-methyl-(6S)-tetrahydrofolic acid of the present invention has a PXRD pattern with at least one characteristic peak (expressed in $2\theta \pm 0.3°2\theta$ (CuKα radiation)) at 3.2, 6.4, 7.8, 9.6, 12.7, 13.3, 13.9, 14.2, 14.7, 15.6, 16.3, 16.7, 17.2, 17.8, 18.2, 18.5, 19.3, 19.6, and 20.3.

Even more preferred, the crystalline sodium salt of 5-methyl-(6S)-tetrahydrofolic acid of the present invention has a PXRD pattern with at least two, even more preferred at least three, most preferred at least four, preferably at least five, more preferred at least six and most preferred has characteristic peaks (expressed in $2\theta \pm 0.3°2\theta$ (CuKα radiation)) at 3.2, 6.4, 7.8, 9.6, 12.7, 13.3, 13.9, 14.2, 14.7, 15.6, 16.3, 16.7, 17.2, 17.8, 18.2, 18.5, 19.3, 19.6, and 20.3.

Preferably, the crystalline sodium salt of 5-methyl-(6S)-tetrahydrofolic acid of the present invention has a PXRD pattern with at least one characteristic peak (expressed in $2\theta \pm 0.3°2\theta$ (CuKα radiation)) at 3.2, 6.4, 7.8, 9.6, 12.7, 13.3, 13.9, 14.2, 14.7, 15.6, 16.3, 16.7, 17.2, 17.8, 18.2, 18.5, 19.3, 19.6, 20.0, 20.3, 20.7, 21.5, 22.0, 22.9, 23.5, 24.0, 24.6, 25.0, 25.4, 27.2 and 28.7.

Even more preferred, the crystalline sodium salt of 5-methyl-(6S)-tetrahydrofolic acid of the present invention has a PXRD pattern with at least two, even more preferred at least three, most preferred at least four, preferably at least five, more preferred at least six and most preferred has characteristic peaks (expressed in $2\theta \pm 0.3°2\theta$ (CuKα radiation)) at 3.2, 6.4, 7.8, 9.6, 12.7, 13.3, 13.9, 14.2, 14.7, 15.6, 16.3, 16.7, 17.2, 17.8, 18.2, 18.5, 19.3, 19.6, 20.0, 20.3, 20.7, 21.5, 22.0, 22.9, 23.5, 24.0, 24.6, 25.0, 25.4, 27.2 and 28.7.

Preferably, the sodium salt of 5-methyl-(6S)-tetrahydrofolic acid of the present invention has a PXRD pattern substantially as shown in FIG. 1, FIG. 2 and/or FIG. 4.

A further aspect of the invention is that the crystalline sodium salt of 5-methyl-(6S)-tetrahydrofolic acid having a Raman spectrum with least one characteristic peak (expressed in wavenumbers, $cm^{-1}$, with an experimental uncertainty of ±1-2 $cm^{-1}$) at 3055, 2929, 1611, 1582, 1536, 1483, 1462, 1418, 1381, 1329, 1311, 1276, 1192, 1021, 949, 875, 835, 776, 651, 621, 479 and 363 $cm^{-1}$.

Yet a further aspect of the present invention is that the crystalline sodium salt of 5-methyl-(6S)-tetrahydrofolic acid according to the present invention exhibits a Raman spectrum substantially as depicted in FIG. 3.

A further aspect of the present invention is a process for obtaining the crystalline sodium salt of 5-methyl-(6S)-tetrahydrofolic acid according to the present invention comprising the steps of:

a) providing of 5-methyl-(6S)-tetrahydrofolic acid, optionally in a suitable solvent or a mixture of solvents;
b) adding sodium hydroxide to the composition of step a);
c) optionally adding a solvent, mixture of solvents and/or a co-salt former to the composition of step b), or adding the composition of step b) to a solvent, a mixture of solvents and/or a co-salt former;
d) crystallizing;
e) optionally adding more solvent or mixture of solvents; and
f) isolating the obtained solid.

Preferably, the molar ratio of 5-methyl-(6S)-tetrahydrofolic acid and sodium hydroxide in step b) is in the range of from 1:1.9 to 1:3.

Preferably, the solvent and/or mixtures of solvents according to step a), c) and/or e) is selected from the group consisting of water, water-soluble alcohols, methanol, ethanol, isopropanol, n-propanol, acetonitrile, tetrahydrofuran, acetone, methyl ethyl ketone, methyl isobutyl ketone, benzylalcohol, and mixtures thereof.

A co-salt former as used herein is a chemical substance that facilitates the formation of the crystalline sodium salt according to the present invention. Co-salt formers according to the present invention are typically organic bases that are sufficiently soluble in the process solvents so that they are removed in the filtration step or can be easily washed off after filtration.

Preferably, the co-salt former in step c) is an organic base with a pKa value from 6 to 11 and even more preferred with a pKa value from 7 to 10.

Even more preferred, in step d) the temperature is at least 15° C.

Preferably, in step a), b), c) and/or d) seed crystals are added. Even more preferred the seed crystals are the desired sodium salt of 5-methyl-(6S)-tetrahydrofolic acid.

A further aspect of the present invention is a pharmaceutical composition, food additive vitamin and/or other preparation comprising the crystalline sodium salt of 5-methyl-(6S)-tetrahydrofolic acid according to the present invention and optionally one or more acceptable excipients and the use of the crystalline sodium salt of 5-methyl-(6S)-tetrahydrofolic acid according to the present invention as constituent for the production of drugs and/or food additives.

The crystalline sodium salt of 5-methyl-(6S)-tetrahydrofolic acid of the present invention for use in homocysteine-lowering, the treatment of anemia, neural tube defects, cardiovascular diseases, depression, Alzheimer's disease, cognitive impairment and osteoporosis and/or dietary management of low plasma and/or low red blood cell folate and/or low cerebrospinal fluid folate and/or low peripheral or central nervous system folate is also part of the present invention.

Surprisingly, the crystalline sodium salt of 5-methyl-(6S)-tetrahydrofolic acid of the present invention has an improved kinetic solubility compared with the crystalline calcium salt disclosed in U.S. Pat. No. 6,441,168 B1. The measurement of the kinetic solubility was conducted as described in the experimental part.

The solubility of the crystalline sodium salt of 5-methyl-(6S)-tetrahydrofolic acid of the present invention in water (room temperature) is greater than 100 mg per 1 ml of water, whereas the calcium salt exhibits a solubility being considerably smaller than 10 mg per 1 ml of water.

Due to the higher solubility of the sodium salt of the present invention the bioavailability is much better. This results in oral dosage forms, in which the amount of the active ingredient can be reduced, without diminishing the effectivity of the medicament or food additive.

Pharmaceutical compositions according to the present invention can be applied for all modes of administration, preferably for oral, parenteral, intramuscular, intraspinal, intrathecal, peridontal, topical or rectal administration.

In summary, the profile of properties offered by the crystalline sodium salt of 5-methyl-(6S)-tetrahydrofolic acid of the present invention is advantageous for use in medicaments or as food additive.

EXPERIMENTAL

Powder X-Ray Diffraction

Stoe Stadi P equipped with a Mythen1K Detector; Cu-Kα1 radiation; standard measurement conditions: transmission; 40 kV and 40 mA tube power; curved Ge monochromator; 0.02°2θ step size, 48 s step time, 1.5-50.5°2θ scanning range; detector mode: step scan; 1°2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

Raman Spectroscopy

FT-Raman spectra were recorded on a Bruker MultiRAM FT-Raman or a Bruker RFS 100 FT-Raman system with a near infrared Nd:YAG laser operating at 1064 nm and a liquid nitrogen-cooled germanium detector. 64 scans with a resolution of 2 cm$^{-1}$ were accumulated in the range from 3500 to −50 cm$^{-1}$; however, only data above 100 cm$^{-1}$ are evaluated due to filter cutoff effects. Nominal laser powers are typically 100 or 300 mW.

TG-FTIR

Thermogravimetric measurements were carried out with a Netzsch Thermo-Microbalance TG 209 coupled to a Bruker FTIR Spectrometer Vector 22 (sample pans with a pinhole, N$_2$ atmosphere, heating rate 10 K/min).

Example 1: Crystalline Sodium Salt of 5-methyl-(6S)-tetrahydrofolic acid Produced from Amorphous Disodium Salt of 5-methyl-(6S)-tetrahydrofolic acid (Seeding with Calcium Salt of 5-methyl-(6S)-tetrahydrofolic acid)

Figure 1:
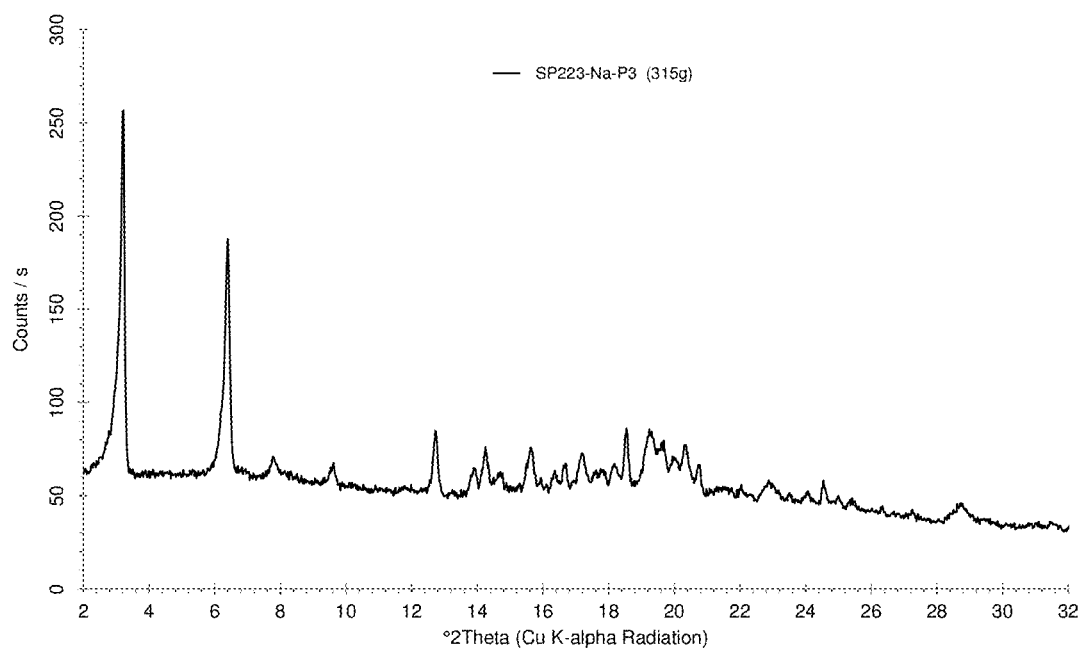
FIG. 1: PXRD of the crystalline sodium salt of 5-methyl-(6S)-tetrahydrofolic acid according to Example 1
Figure 3:
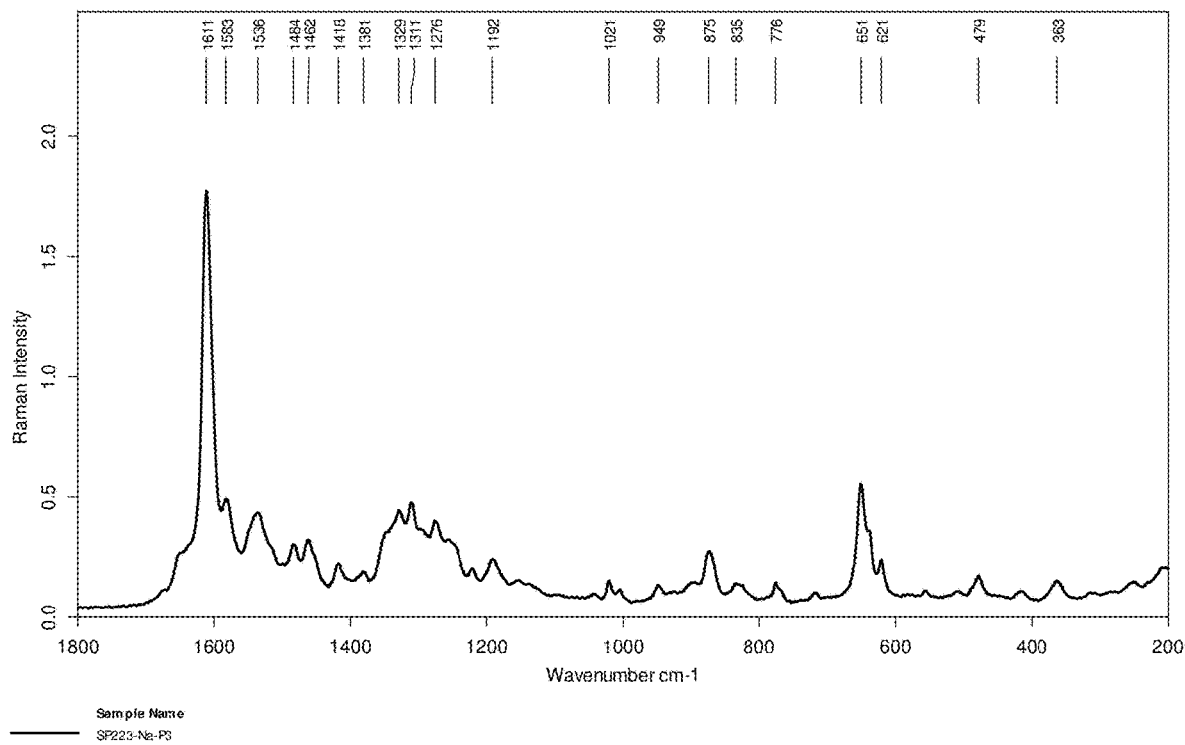
FIG. 3: Raman spectrum the crystalline sodium salt of 5-methyl-(6S)-tetrahydrofolic acid according to Example 1

250.9 mg of amorphous 5-methyl-(6S)-tetrahydrofolic acid disodium salt were weighed into a 22 mL Supelco glass vial equipped with a magnetic stirrer bar. 2.0 mL of ethanol were added. The sample was sonicated for 1 minute and stirred at room temperature for 12 minutes. The gas phase of the vial was purged for 1 minute with nitrogen (about 100 mL/min). The sample was then stirred at 80° C. for 10 minutes. 3.0 mL of ethanol was added (in total 5.0 ml ethanol) and 0.5 mL of water were added (water activity about 0.50). The sample was sonicated for about 10 seconds at room temperature and stirred again at 80° C. for 5 minutes. The sample was seeded with about 1 mg of crystalline calcium salt of 5-methyl-(6S)-tetrahydrofolic acid and stirred at 80° C. for 3 minutes. An off-white suspension was formed and solid material that adhered to the glass wall of the vial was scraped off a spatula and a yellow suspension was formed. The suspension was stirred at 80° C. for about 17 minutes and the solid material was again scraped from the glass wall using a spatula. The suspension was easy to stir. To the orange suspension, 3.0 mL of acetonitrile were added and the suspension was then stirred at 80° C. for 30 minutes. Hot filtration was carried out. The suspension was filtered using a fritted glass filter (porosity P4, Ø 1 cm) and the filter cake was air dried for 3 minutes. The filter cake was then transferred into weighing paper and further air dried for about 12 minutes at a relative humidity of about 40%. The solid product was 178 mg of a fine yellowish powder. Characterization by light microscopy and PXRD confirmed the crystalline nature of the solid. H-NMR spectroscopy confirmed the chemical integrity of 5-methyl-(6S)-tetrahydrofolic acid. The solid product shows a PXRD pattern as shown in FIG. 1 with peak locations as listed in Table 1. Further examination by Raman spectroscopy shows that the sample exhibits a Raman spectrum as depicted in FIG. 3 with peak positions as presented in Table 2.

TABLE 1

Powder X-ray diffraction data for crystalline sodium salt of Example 1 with 2-theta angles, d-spacing values in Ångstrom and qualitative intensity values as follows: vs = very strong, s = strong, m = medium, w = weak and vw = very weak.

| ° 2-theta | d-spacings [Å] | intensity (qualitative) |
|---|---|---|
| 3.2 | 27.6 | vs |
| 6.4 | 13.8 | vs |
| 7.8 | 11.3 | m |
| 9.6 | 9.2 | m |
| 12.7 | 7.0 | s |
| 13.3 | 6.7 | m |
| 13.9 | 6.4 | m |
| 14.2 | 6.2 | m |
| 14.7 | 6.0 | m |
| 15.6 | 5.67 | m |
| 16.3 | 5.42 | m |
| 16.7 | 5.32 | m |
| 17.2 | 5.16 | m |
| 17.8 | 4.98 | m |
| 18.2 | 4.88 | m |
| 18.5 | 4.78 | s |
| 19.3 | 4.60 | s |
| 19.6 | 4.52 | s |
| 20.0 | 4.44 | m |
| 20.3 | 4.37 | s |
| 20.7 | 4.28 | m |
| 21.5 | 4.12 | m |
| 22.0 | 4.03 | m |
| 22.9 | 3.88 | m |
| 23.5 | 3.78 | m |
| 24.0 | 3.70 | m |
| 24.6 | 3.62 | m |
| 25.0 | 3.56 | m |
| 25.4 | 3.50 | m |

TABLE 2

Raman data for the crystalline sodium salt of Example 1 with wavenumber in cm$^{-1}$ and intensity values. It should be noted that the intensities vary with Laser power, sample amount and other factors.

| wavenumber (cm$^{-1}$) | intensity (arbitrary units) |
|---|---|
| 3055 | 0.15 |
| 2929 | 0.32 |
| 1611 | 1.78 |
| 1582 | 0.49 |
| 1536 | 0.44 |
| 1483 | 0.30 |
| 1462 | 0.32 |
| 1418 | 0.22 |
| 1381 | 0.19 |
| 1329 | 0.44 |
| 1311 | 0.48 |
| 1276 | 0.40 |
| 1192 | 0.24 |
| 1021 | 0.15 |
| 949 | 0.14 |
| 875 | 0.28 |
| 835 | 0.14 |
| 776 | 0.15 |
| 651 | 0.55 |
| 621 | 0.24 |
| 479 | 0.17 |
| 363 | 0.15 |

Example 2: Crystalline Sodium Salt of 5-methyl-(6S)-tetrahydrofolic acid Produced from Amorphous Disodium Salt of 5-methyl-(6S)-tetrahydrofolic acid (Seeding with Crystalline Monosodium Salt of 5-methyl-(6S)-tetrahydrofolic acid)

1.2055 g of amorphous 5-methyl-(6S)-tetrahydrofolic acid disodium salt were weighed into a 40 mL Supelco glass vial equipped with a magnetic stirrer bar. 10.0 mL of ethanol/water 10:1 v/v were added. The suspension was stirred at room temperature for 8 minutes and seeded with 12 mg of crystalline monosodium salt of 5-methyl-(6S)-tetrahydrofolic acid. The suspension was stirred at room temperature for 5 minutes and the gas phase of the vial was purged for 1 minute with nitrogen (about 100 mL/min). An additional 10 mL of ethanol/water 10:1 v/v (water activity about 0.50) were added. The suspension was now easy to stir. It was sonicated for 1 minute and stirred at room temperature for 50 minutes. Microscopy of the suspension showed the presence of amorphous material. The gas phase of the vial was again purged for 1 minute with nitrogen (about 100 mL/min). The sample was then stirred at about 70° C. for 10 minutes. The sample was further stirred at about 70° C. for 10 minutes, seeded again with crystalline monosodium salt of 5-methyl-(6S)-tetrahydrofolic acid and stirred at about 70° C. for 8 minutes. A very weak suspension was formed. Stirring was continued at 70° C. for about 3 hours until a suspension formed that did not contain sticky amorphous solid as part of the mixture. As soon as an in-process control by light microscopy showed that the sample was predominantly crystalline hot filtration was carried out. The filter cake was air dried for 15 minutes. The fine, yellowish powder (0.8424 g) was examined by TG-FTIR. Since the mass loss was 15.4% (water and some ethanol) the sample was transferred into a 15 mL Supelco vial and further dried at room temperature and about 10 mbar for 20 minutes. About 800 mg of a fine, yellowish powder was obtained. Characterization by light microscopy and PXRD confirmed the crystalline nature of the solid. H-NMR spectroscopy confirmed the chemical integrity of 5-methyl-(6S)-tetrahydrofolic acid.

Example 3: Kinetic Solubility of Crystalline Sodium Salt of 5-methyl-(6S)-tetrahydrofolic acid 50 mg of crystalline sodium salt of 5-methyl-(6S)-tetrahydrofolic acid (according to Example 1) is weighed into a 4 ml glass vial with screw cap. Then 0.5 ml of purified/de-ionized water is added. The mixture is vigorously agitated at room temperature and briefly sonicated and a clear slightly yellow solution is readily obtained (within a few seconds). Thus the solubility is greater than 100 mg per 1 ml of water. The solution remains clear for several hours at r.t.

Reference Example 4: Kinetic Solubility of the Calcium Salt of 5-methyl-(6S)-tetrahydrofolic acid 27.9 mg of crystalline calcium salt of 5-methyl-(6S)-tetrahydrofolic acid (containing about 11% of water, thus corresponding to a dry weight of about 25 mg) are weighed into a 4 ml glass vial with screw cap. 2.535 ml of purified/de-ionized water is added to the solid using an adjustable volumetric pipette. The mixture is vigorously agitated at room temperature and briefly sonicated. No clear solution can be obtained and a fairly concentrated suspension persists. Thus the kinetic solubility measured as described here is smaller than 10 mg per 1 ml of water.

Figure 4:
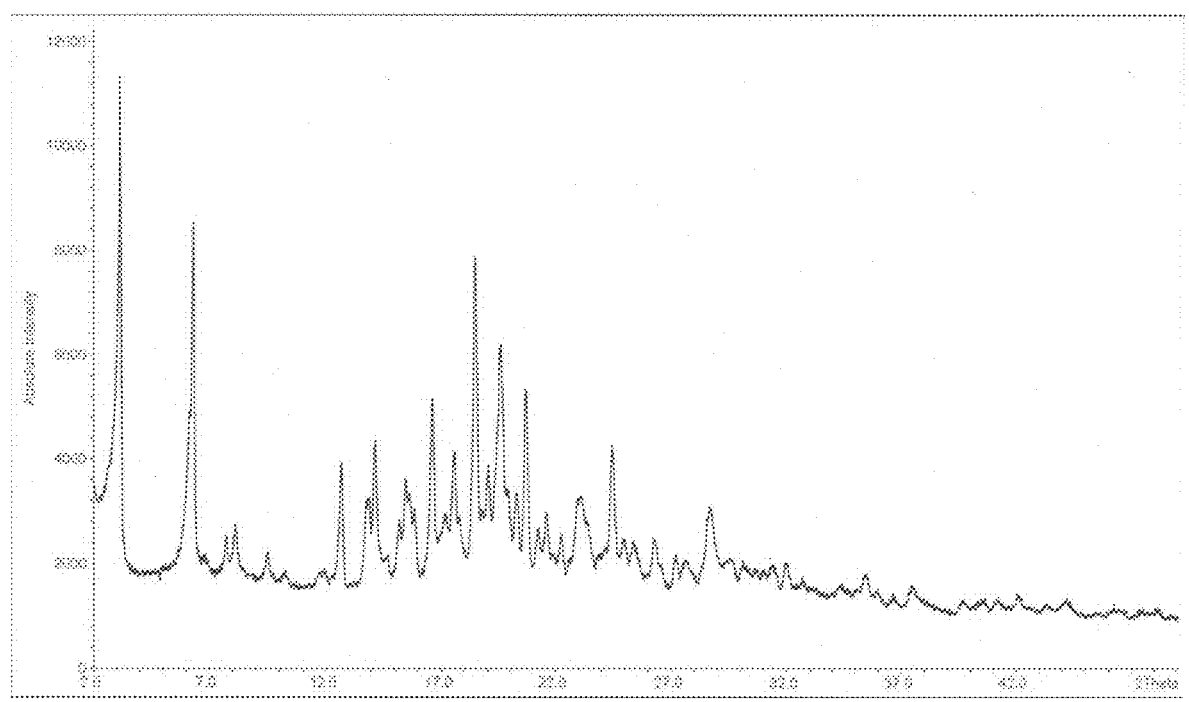
FIG. 4: PXRD of the crystalline sodium salt of 5-methyl-(6S)-tetrahydrofolic acid according to Example 5

Example 5: Preparation of the Crystalline Disodium Salt of 5-methyl-(6S)-tetrahydrofolic acid Starting from 5-methyl-(6S)-tetrahydrofolic acid A mixture of 10 g 5-methyl-(6S)-tetrahydrofolic acid (assay 5-methyltetrahydrofolic acid 95.59% w/w), 20 g water and 1.74 g sodium hydroxide was heated in a glass vessel under a nitrogen atmosphere to 72° C. while stirring. At 72° C. 200 mL ethanol/5% v/v 2-propanol were added within 3.5 hours. Then 0.05 g of crystalline disodium salt of 5-methyl-(6S)-tetrahydrofolic acid were added as seeding material. At 72° C. additional 100 mL ethanol/5% v/v 2-propanol were added within 3 hours. The mixture was cooled to 25° C. within 14 hours and heated again to 72° C. The mixture was treated with ultrasonic to remove material which was sticking to the wall of the glass vessel, while the temperature decreased to 63° C. The solids were separated by filtration with nitrogen pressure in a closed filtration tube and washed with 100 mL ethanol/5% v/v 2-propanol. The solids were dried for 14 hours in vacuum at 36° C. to give 11.03 g of an off-white powder corresponding to 94.5% yield (assay 5-methyltetrahydrofolic acid 81.86% w/w). The solid product shows a PXRD pattern as shown in FIG. 4. PXRD confirmed the crystalline nature of the sample and H-NMR spectroscopy was in agreement with the chemical integrity of 5-methyl-(6S)-tetrahydrofolic acid. Further investigation by TGA (Thermogravimetric Analysis) revealed a mass loss of about 6.1%. The sodium content found by IC (Ion chromatography) was 8.0% which is in good agreement with a disodium salt. HPLC showed a purity of 97.4%.

Reference Example 6: Preparation of the Amorphous Monosodium Salt of 5-methyl-(6S)-tetrahydrofolic acid 6.0 g of crystalline 5-methyl-(6S)-tetrahydrofolic acid monosodium salt prepared according to EP 17164349.7 were added at room temperature to 600 g water. Solids were removed by suction filtration. The filtrate was frozen in a bath with liquid nitrogen and lyophilized in vacuum at 0.07 mbar. After 2 days the vacuum was replaced by nitrogen gas. 6.0 g amorphous 5-methyl-(6S)-tetrahydrofolic acid monosodium salt were obtained with a purity of 95.2% area, water content 8.8% w/w, assay sodium 4.5% w/w.

Figure 5:
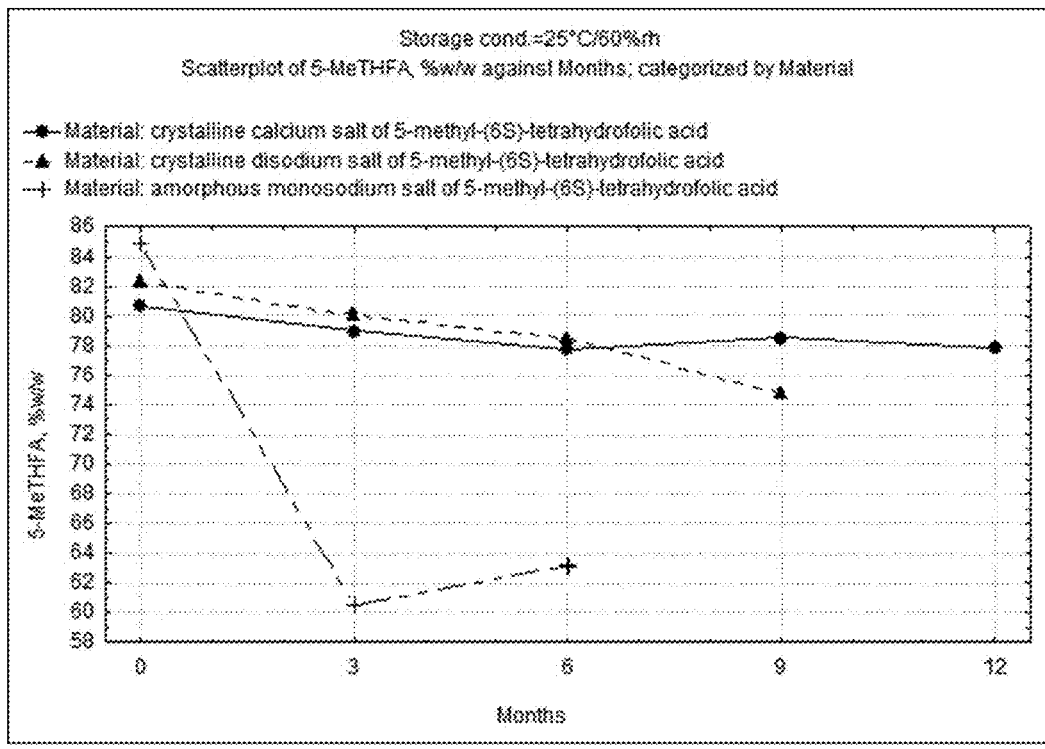
FIG. 5: Long-term stability of the crystalline sodium salt of 5-methyl-(6S)-tetrahydrofolic acid at 25° C./60% rh (% w/w)
Figure 6:
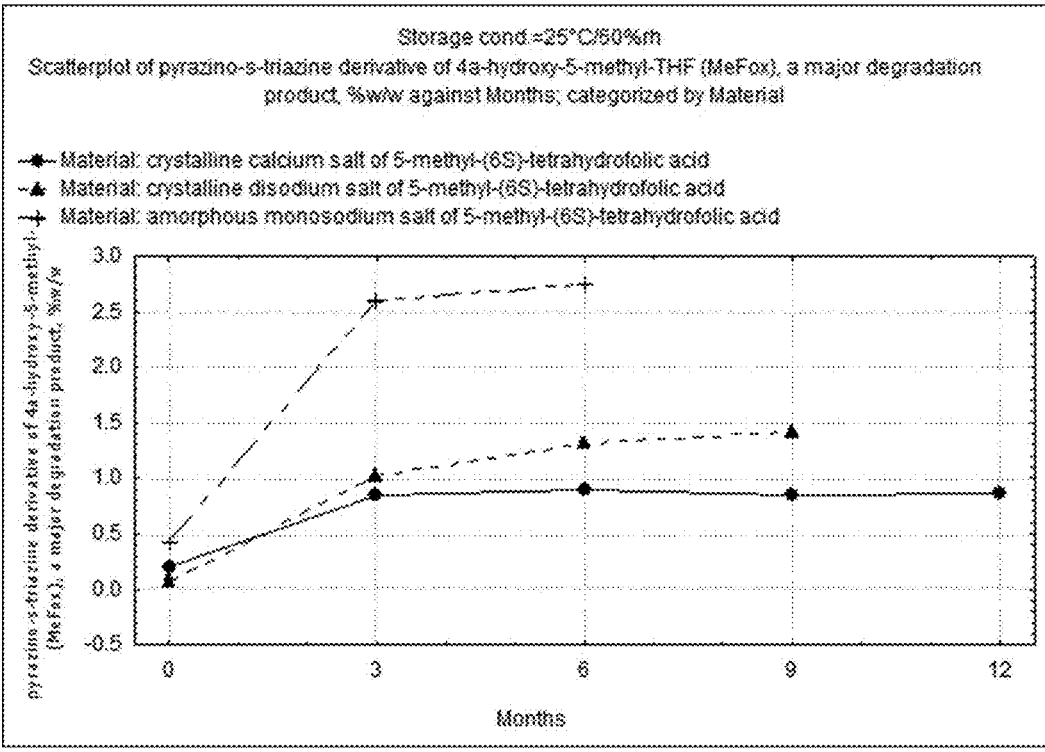
FIG. 6: Long-term stability of the crystalline sodium salt of 5-methyl-(6S)-tetrahydrofolic acid at 25° C./60% rh (major degradation product [MeFox]) (% w/w)

Example 7: Stability of the Crystalline Sodium Salt of 5-methyl-(6S)-tetrahydrofolic acid In order to compare the long-term stabilities of the crystalline sodium salt of 5-methyl-(6S)-tetrahydrofolic acid, the compounds of the invention, to the long-term stability of the amorphous monosodium salt of 5-methyl-(6S)-tetrahydrofolic acid prepared according to Reference Example 6 and the crystalline calcium salt of 5-methyl-(6S)-tetrahydrofolic acid as prepared according to EP 1 044 975 B1, respective stability data has been generated at various temperatures and humidities.
(a) Stability of the Crystalline Sodium Salt of 5-methyl-(6S)-tetrahydrofolic acid at 25° C./60% rh
Amorphous monosodium salt of 5-methyl-(6S)-tetrahydrofolic acid prepared according to Reference Example 6, crystalline calcium salt of 5-methyl-(6S)-tetrahydrofolic acid, prepared according to literature procedures (EP 1 044 975 B1) and crystalline sodium salt of 5-methyl-(6S)-tetrahydrofolic acid, prepared as disclosed in Example 1, were stored at 25° C./60% rh. The content of 5-methyl-(6S)-tetrahydrofolic acid remaining in the samples was measured by HPLC at periodic intervals (% w/w). The results are shown in Table 1a and FIG. 5. The content of 5-methyl-(6S)-tetrahydrofolic acid remaining was also compared to the initial value at the time of preparation (% rel.). The results are shown in Tables 1 b. Additionally the content of the pyrazino-s-triazine derivative of 4α-hydroxy-5-methyl- THF (MeFox), a major degradation product, was measured by HPLC at periodic intervals and disclosed as absolute values (% w/w). The results are shown in Table 2 and FIG. 6.

TABLE 1a

Long-term stability of the crystalline sodium salt of 5-methyl-(6S)-tetrahydrofolic acid at 25° C./60% rh (% w/w)

| | 5-methyl-(6S)-tetrahydrofolic acid (% w/w) | | | | |
|---|---|---|---|---|---|
| | 0 months | 3 months | 6 months | 9 months | 12 months |
| amorphous monosodium salt of 5-methyl-(6S)-tetrahydrofolic acid | 84.9 | 60.6 | 63.2 | | |
| crystalline sodium salt of 5-methyl-(6S)-tetrahydrofolic acid | 82.3 | 80.0 | 78.6 | 74.7 | |
| crystalline calcium salt of 5-methyl-(6S)-tetrahydrofolic acid | 80.7 | 79.0 | 77.7 | 78.5 | 77.9 |

TABLE 1b

Long-term stability of the crystalline monosodium salt of 5-methyl-(6S)-tetrahydrofolic acid at 25° C./60% rh (% rel.)

| | 5-methyl-(6S)-tetrahydrofolic acid (% rel.) | | | | |
|---|---|---|---|---|---|
| | 0 months | 3 months | 6 months | 9 months | 12 months |
| amorphous monosodium salt of 5-methyl-(6S)-tetrahydrofolic acid | 100.0 | 71.3 | 74.5 | | |
| crystalline sodium salt of 5-methyl-(6S)-tetrahydrofolic acid | 100.0 | 97.3 | 95.5 | 90.8 | |
| crystalline calcium salt of 5-methyl-(6S)-tetrahydrofolic acid | 100.0 | 97.9 | 96.3 | 97.3 | 96.5 |

TABLE 2

Long-term stability of the crystalline sodium salt of 5-methyl-(6S)-tetrahydrofolic acid at 25° C./60% rh (major degradation product [MeFox])

| | Pyrazino-s-triazine derivative of 4α-hydroxy-5-methyl-THF (MeFox) (% w/w) | | | | |
|---|---|---|---|---|---|
| | 0 months | 3 months | 6 months | 9 months | 12 months |
| amorphous monosodium salt of 5-methyl-(6S)-tetrahydrofolic acid | 0.43 | 2.60 | 2.75 | | |
| crystalline monosodium salt of 5-methyl-(6S)-tetrahydrofolic acid | 0.07 | 1.01 | 1.31 | 1.42 | |
| crystalline calcium salt of 5-methyl-(6S)-tetrahydrofolic acid | 0.20 | 0.84 | 0.90 | 0.85 | 0.86 |

Figure 7:
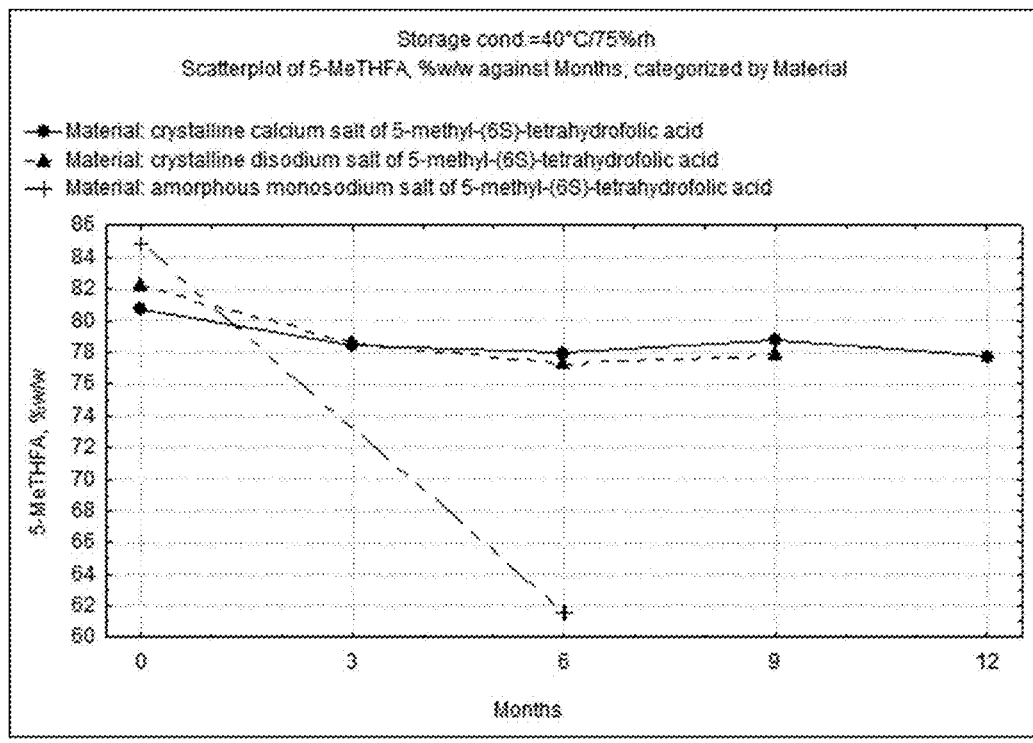
FIG. 7: Long-term stability of the crystalline sodium salt of 5-methyl-(6S)-tetrahydrofolic acid at 40° C./75% rh (% w/w)
Figure 8:
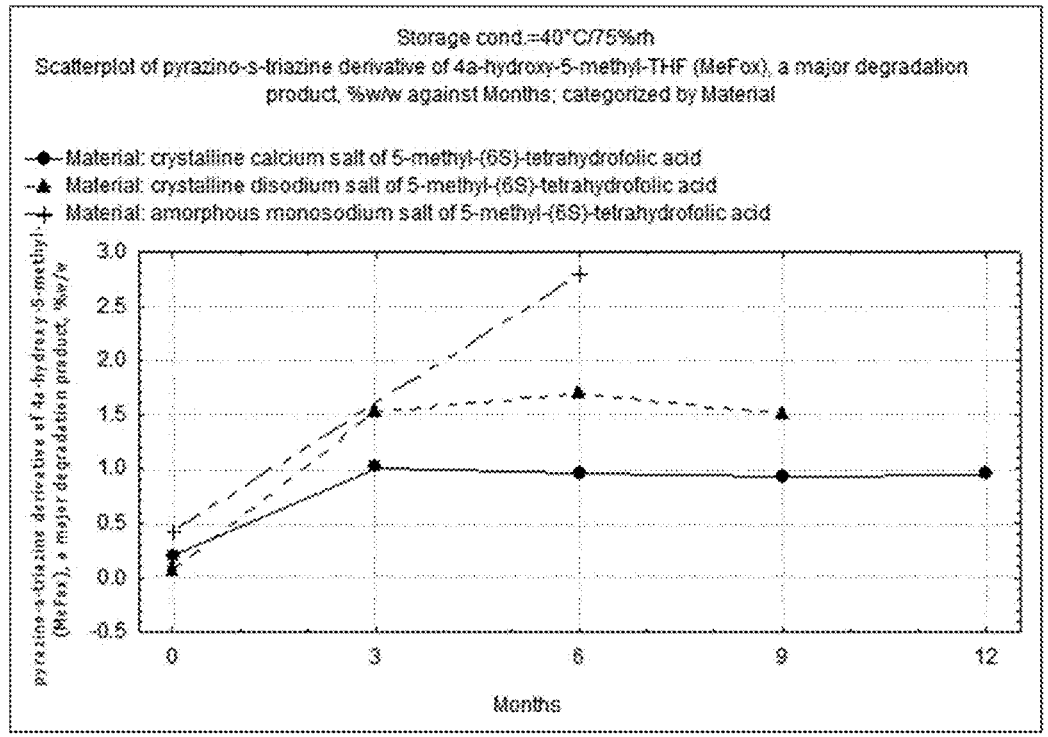
FIG. 8: Long-term stability of the crystalline sodium salt of 5-methyl-(6S)-tetrahydrofolic acid at 40° C./75% rh (major degradation product [MeFox]) (% w/w)

(b) Stability of the Crystalline Sodium Salt of 5-methyl-(6S)-tetrahydrofolic acid at 40° C./75% rh Amorphous monosodium salt of 5-methyl-(6S)-tetrahydrofolic acid prepared according to Reference Example 6, crystalline calcium salt of 5-methyl-(6S)-tetrahydrofolic acid, prepared according to literature procedures (EP 1 044 975 B1) and crystalline sodium salt of 5-methyl-(6S)-tetrahydrofolic acid, prepared as disclosed in Example 1, were stored at 40° C./75% rh. The content of 5-methyl-(6S)-tetrahydrofolic acid remaining in the sample was measured by HPLC at periodic intervals (% w/w). The results are shown in Table 3a and FIG. 7. The content of 5-methyl-(6S)-tetrahydrofolic acid remaining was also compared to the initial value at the time of preparation (% rel.). The results are shown in Tables 3b. Additionally the content of the pyrazino-s-triazine derivative of 4α-hydroxy-5-methyl-THF (MeFox), a major degradation product, was measured by HPLC at periodic intervals and disclosed as absolute values (% w/w). The results are shown in Table 4 and FIG. 8.

TABLE 3a

Long-term stability of the crystalline sodium salt of 5-methyl-(6S)-tetrahydrofolic acid at 40° C./75% rh (% w/w)

| | 5-methyl-(6S)-tetrahydrofolic acid (% w/w) | | | | |
|---|---|---|---|---|---|
| | 0 months | 3 months | 6 months | 9 months | 12 months |
| amorphous monosodium salt of 5-methyl-(6S)-tetrahydrofolic acid | 84.9 | 61.6 | | | |
| crystalline sodium salt of 5-methyl-(6S)-tetrahydrofolic acid | 82.3 | 78.6 | 77.3 | 77.9 | |
| crystalline calcium salt of 5-methyl-(6S)-tetrahydrofolic acid | 80.7 | 78.5 | 78.0 | 78.8 | 77.8 |

TABLE 3b

Long-term stability of the crystalline monosodium salt of 5-methyl-(6S)-tetrahydrofolic acid at 40° C./75% rh (% rel.)

| | 5-methyl-(6S)-tetrahydrofolic acid (% rel.) | | | | |
|---|---|---|---|---|---|
| | 0 months | 3 months | 6 months | 9 months | 12 months |
| amorphous monosodium salt of 5-methyl-(6S)-tetrahydrofolic acid | 100.0 | 72.6 | | | |
| crystalline sodium salt of 5-methyl-(6S)-tetrahydrofolic acid | 100.0 | 95.6 | 94.0 | 94.7 | |
| crystalline calcium salt of 5-methyl-(6S)-tetrahydrofolic acid | 100.0 | 97.2 | 96.6 | 97.6 | 96.3 |

TABLE 4

Long-term stability of the crystalline sodium salt
of 5-methyl-(6S)-tetrahydrofolic acid at 40°
C./75% rh (major degradation product [MeFox])

| | Pyrazino-s-triazine derivative of 4α-hydroxy-5-methyl-THF (MeFox) (% w/w) | | | | |
|---|---|---|---|---|---|
| | 0 months | 3 months | 6 months | 9 months | 12 months |
| amorphous monosodium salt of 5-methyl-(6S)-tetrahydrofolic acid | 0.43 | 2.79 | | | |
| crystalline sodium salt of 5-methyl-(6S)-tetrahydrofolic acid | 0.07 | 1.52 | 1.69 | 1.51 | |
| crystalline calcium salt of 5-methyl-(6S)-tetrahydrofolic acid | 0.20 | 1.01 | 0.96 | 0.93 | 0.95 |

Tables 1 to 4 with the stability data of crystalline sodium salt of 5-methyl-(6S)-tetrahydrofolic acid as disclosed in in the present invention clearly shows that
i) there is a remarkable difference in the stability of crystalline sodium salt of 5-methyl-(6S)-tetrahydrofolic acid compared to the amorphous monosodium salt crystalline calcium salt of 5-methyl-(6S)-tetrahydrofolic acid and
ii) the crystalline sodium salt of 5-methyl-(6S)-tetrahydrofolic acid is showing a comparable stability over a long period of time to the crystalline calcium salt of 5-methyl-(6S)-tetrahydrofolic acid.

The invention claimed is:

1. A crystalline sodium salt of 5-methyl-(6S)-tetrahydrofolic acid wherein the molar ratio of 5-methyl-(6S)-tetrahydrofolic acid to sodium is from 1:1.51 to 1:2.5 and/or a hydrate and/or a solvate thereof.

2. The crystalline salt of claim 1, wherein the molar ratio of 5-methyl-(6S)-tetrahydrofolic acid to sodium is from 1:1.75 to 1:2.25 and/or hydrates and/or solvates thereof.

3. The crystalline salt of claim 1, wherein the molar ratio of 5-methyl-(6S)-tetrahydrofolic acid to sodium is approximately 1:2 (in mol/mol).

4. The crystalline salt of claim 1, characterized in that the salt is the sodium salt of 5-methyl-(6S)-tetrahydrofolic acid and has a PXRD pattern with at least one characteristic peak (expressed in 2θ±0.3° 2θ(CuKα radiation)) at 3.2, 6.4, 7.8, 9.6, 12.7, 13.3, 13.9, 14.2, 14.7, 15.6, 16.3, 16.7, 17.2, 17.8, 18.2, 18.5, 19.3, 19.6, and 20.3.

5. The crystalline salt of claim 1, characterized in that the salt is the sodium salt of 5-methyl-(6S)-tetrahydrofolic acid and has a PXRD pattern with at least one characteristic peak (expressed in 2θ±0.3° 2θ (CuKα radiation)) at 3.2, 6.4, 7.8, 9.6, 12.7, 13.3, 13.9, 14.2, 14.7, 15.6, 16.3, 16.7, 17.2, 17.8, 18.2, 18.5, 19.3, 19.6, 20.0, 20.3, 20.7, 21.5, 22.0, 22.9, 23.5, 24.0, 24.6, 25.0, 25.4, 27.2 and 28.7.

Figure 2:
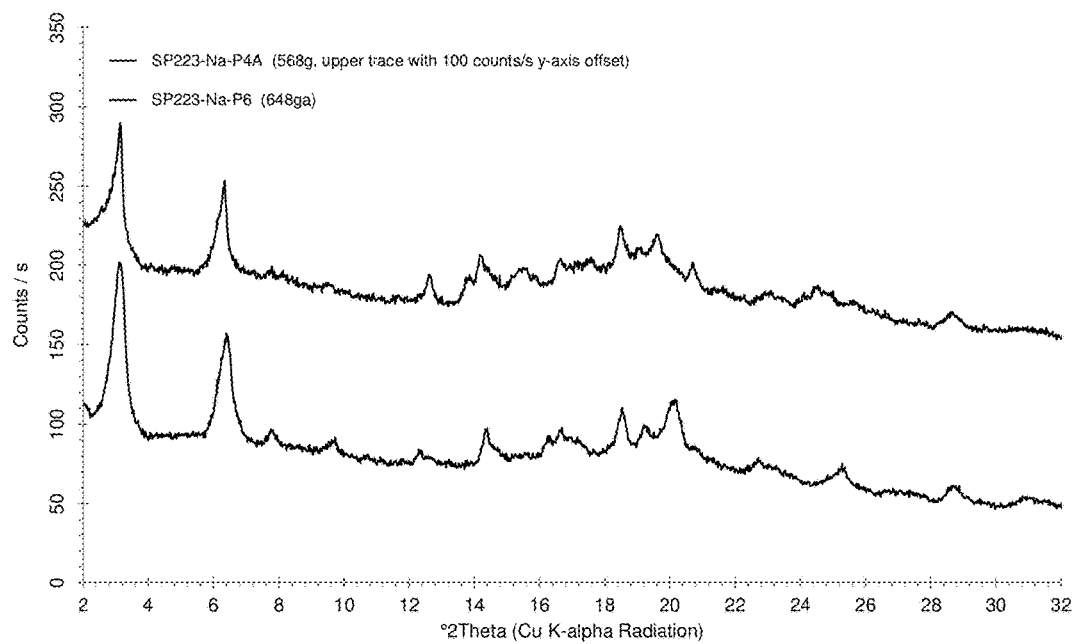
FIG. 2: PXRD of the crystalline sodium salt of 5-methyl-(6S)-tetrahydrofolic acid according to Example 1

6. The crystalline salt of claim 1, characterized in that the sodium salt of 5-methyl-(6S)-tetrahydrofolic acid has a PXRD pattern substantially as shown in FIG. 1, FIG. 2 or FIG. 4.

7. The crystalline according to claim 1, having at least 99% or more chemical and stereoisomerical purity.

8. A process for obtaining the crystalline sodium salt of 5-methyl-(6S)-tetrahydrofolic acid according to claim 1 comprising the steps of:

a) providing of 5-methyl-(6S)-tetrahydrofolic acid, optionally in a suitable solvent or a mixture of solvents;
b) adding sodium hydroxide to the composition of step a);
c) optionally adding a solvent, mixture of solvents and/or a co-salt former to the composition of step b), or adding the composition of step b) to a solvent, a mixture of solvents and/or a co-salt former;
d) crystallizing;
e) optionally adding more solvent or mixture of solvents; and
f) isolating the obtained solid.

9. The process of claim 8, characterized in that the molar ratio of 5-methyl-(6S)-tetrahydrofolic acid and sodium hydroxide in step b) is in the range of from 1:1.51 to 1:5.

10. The process of claim 8, characterized in that the molar ratio of 5-methyl-(6S)-tetrahydrofolic acid and sodium hydroxide in step b) is in the range of from 1:1.9 to 1:3.

11. The process of claim 8, characterized in that solvent and/or mixtures mixture of solvents according to step a), c) and/or e) is selected from the group consisting of water, water-soluble alcohols, acetonitrile, tetrahydrofuran, acetone, methyl ethyl ketone, methyl isobutyl ketone, benzyl alcohol, or a mixture thereof.

12. The process of claim 8, characterized in that the co-salt former of step c) is an organic base with a pKa value from 6 to 11.

13. The process of claim 8, characterized in that the co-salt former of step c) is an organic base with a pKa value from 7 to 10.

14. The process of claim 8, characterized in that in step d) the temperature is at least 15° C.

15. The process of claim 8, characterized in that in step a), b), c) and/or d) seed crystals are added.

16. A pharmaceutical composition, food additive and/or vitamin comprising the crystalline sodium salt of 5-methyl-(6S)-tetrahydrofolic acid according to claim 1 and optionally one or more acceptable excipients.

17. The pharmaceutical composition according to claim 16 in the form of tablets, capsules, oral liquid preparations, powders, lyophilisates, granules, lozenges, reconstitutable powders, injectable or infusable solutions or suspensions or suppositories.

18. The pharmaceutical composition according to claim 16 further comprising at least one additional therapeutic agent.

19. The pharmaceutical composition according to claim 16, which is a pharmaceutical composition for oral, parenteral, intramuscular, intraspinal, intrathecal, periodontal, topical or rectal administration.

20. A method which comprises adding the crystalline sodium salt of 5-methyl-(6S)-tetrahydrofolic acid according to claim 1 to a drug or food additive.

21. A method comprising using the crystalline sodium salt of 5-methyl-(6S)-tetrahydrofolic acid according to claim 1 in homocysteine lowering or in the treatment of anemia or neural tube defects, or in dietary management of low plasma folate, low red blood cell folate, low cerebrospinal fluid folate or low peripheral or central nervous system folate.

22. The process of claim 11, characterized in that a solvent and/or mixture of solvents according to step a), c) and/or e) is a water-soluble alcohol, selected from the group consisting of methanol, ethanol, isopropanol and n-propanol.

* * * * *